(12) United States Patent
Rybalov

(10) Patent No.: US 11,182,558 B2
(45) Date of Patent: Nov. 23, 2021

(54) DEVICE, SYSTEM, AND METHOD FOR DATA ANALYSIS AND DIAGNOSTICS UTILIZING DYNAMIC WORD ENTROPY

(71) Applicant: MOTIV8AI LTD, Tel Aviv (IL)

(72) Inventor: Alexander Rybalov, Psagot (IL)

(73) Assignee: MOTIV8AI LDT, Tel Aviv (IL)

( * ) Notice: Subject to any disclaimer, the term of this patent is extended or adjusted under 35 U.S.C. 154(b) by 152 days.

(21) Appl. No.: 16/283,773

(22) Filed: Feb. 24, 2019

(65) Prior Publication Data

US 2020/0272694 A1 Aug. 27, 2020

(51) Int. Cl.
| | |
|---|---|
| G06F 40/30 | (2020.01) |
| A61B 5/00 | (2006.01) |
| A61B 5/16 | (2006.01) |
| G06F 40/279 | (2020.01) |
| A61B 5/145 | (2006.01) |

(52) U.S. Cl.
CPC .............. G06F 40/30 (2020.01); A61B 5/165 (2013.01); A61B 5/4088 (2013.01); A61B 5/4803 (2013.01); A61B 5/7282 (2013.01); G06F 40/279 (2020.01); A61B 5/14532 (2013.01)

(58) Field of Classification Search
CPC ........ G06F 40/30; G06F 40/279; G06F 40/56; G06F 40/253; G06F 40/284; G06F 40/20; G06F 40/289; G06F 40/44; G06F 16/3329; G06F 16/3344; G06F 16/338; G06F 16/367; G06F 40/205; G06F 40/35; G06N 20/00; G06N 3/08; G10L 15/26; G10L 13/00; G10L 15/005; G10L 15/08; G10L 13/02; G10L 13/10; G10L 15/1822; G10L 15/07

See application file for complete search history.

(56) References Cited

U.S. PATENT DOCUMENTS

| | | | | |
|---|---|---|---|---|
| 8,818,789 B2 * | 8/2014 | Abir | ....................... | G06N 5/022 |
| | | | | 704/2 |
| 10,902,737 B2 * | 1/2021 | Tapuhi | ............... | G06Q 10/0639 |
| 2011/0264997 A1 * | 10/2011 | Mukerjee | ............ | G06F 16/3334 |
| | | | | 715/256 |
| 2016/0140114 A1 * | 5/2016 | Orsini | ................... | G06F 40/232 |
| | | | | 704/2 |

* cited by examiner

*Primary Examiner* — Linda Wong
(74) *Attorney, Agent, or Firm* — Browdy and Neimark, P.L.L.C.

(57) ABSTRACT

Devices, systems, and methods for data analysis and diagnostics utilizing Dynamic Word Entropy. A method includes: obtaining a text of a user; determining word entropy values which correspond to different lengths of text-portions of the text of the user; generating a Dynamic Word Entropy table which corresponds to the text of the user; analyzing the table, and determining whether or not the user has a particular medical condition, or determining whether or not a particular intervention has positively affected the user or has negatively affected the user or has not affected the user.

19 Claims, 2 Drawing Sheets

DEVICE, SYSTEM, AND METHOD FOR DATA ANALYSIS AND DIAGNOSTICS UTILIZING DYNAMIC WORD ENTROPY

FIELD

The present invention is related to the field of Information Technology.

BACKGROUND

Millions of people utilize mobile and non-mobile electronic devices, such as smartphones, tablets, laptop computers and desktop computers, in order to perform various activities. Such activities may include, for example, browsing the Internet, sending and receiving electronic mail (email) messages, taking photographs and videos, engaging in a video conference or a chat session, playing games, or the like.

SUMMARY

The present invention may include, for example, systems, devices, and methods for analysis of data and/or performing diagnostics by dynamic word entropy. For example, a method includes: obtaining a text of a user; determining word entropy values which correspond to different lengths of text-portions of the text of the user; generating a Dynamic Word Entropy (DWE) table which corresponds to the text of the user; analyzing the DWE table, and determining whether or not the user has a particular medical condition, or determining whether or not a particular intervention has positively affected the user or has negatively affected the user or has not affected the user.

The present invention may provide other and/or additional benefits or advantages.

DETAILED DESCRIPTION OF SOME DEMONSTRATIVE EMBODIMENTS

The term "text" as used herein may include, for example, a text or text-portion or text-segment, that was uttered or spoken or said by a person, or that was written or typed by a person using a mechanical tool (e.g., pen, pencil) and/or an electronic or digital tool (e.g., computer, smartphone, tablet), or that was dictated to a machine and was then transcribed by the machine, or that was dictated to another person who transcribed it, or that was captured or acquired via an acoustic microphone and was then transcribed by a human transcribing operation or by a machine-based automatic transcription processes such as speech-to-text conversion or Speech Recognition (SR) or Automatic Speech Recognition (ASR), or text that was scanned from a hand-written or printed item (e.g., paper) and was then processed via Optical Character Recognition (OCR) or other methods that extract text from such item(s).

The present invention includes systems and methods that utilize word entropy of text or speech, and particularly the analysis of Dynamic Word Entropy (DWE) of text or speech, as a measure or indicator or signal for the richness or depth of such text or speech, and/or for deducing or estimating or determining one or more properties or characteristics of a human user who generated (e.g., spoke, uttered, wrote, typed, dictated) such text or speech, and/or for deducing or estimating or determining whether a particular treatment (e.g., medical treatment, administration of a medicine or a drug, therapeutic treatment, learning session, focusing session, psychotherapy treatment, behavioral treatment, or the like) has contributed to increase, to decrease, or to not affect the richness or depth (or consistency, or inconsistency, or other characteristics) of such text or speech generated by that person.

Figure 1:
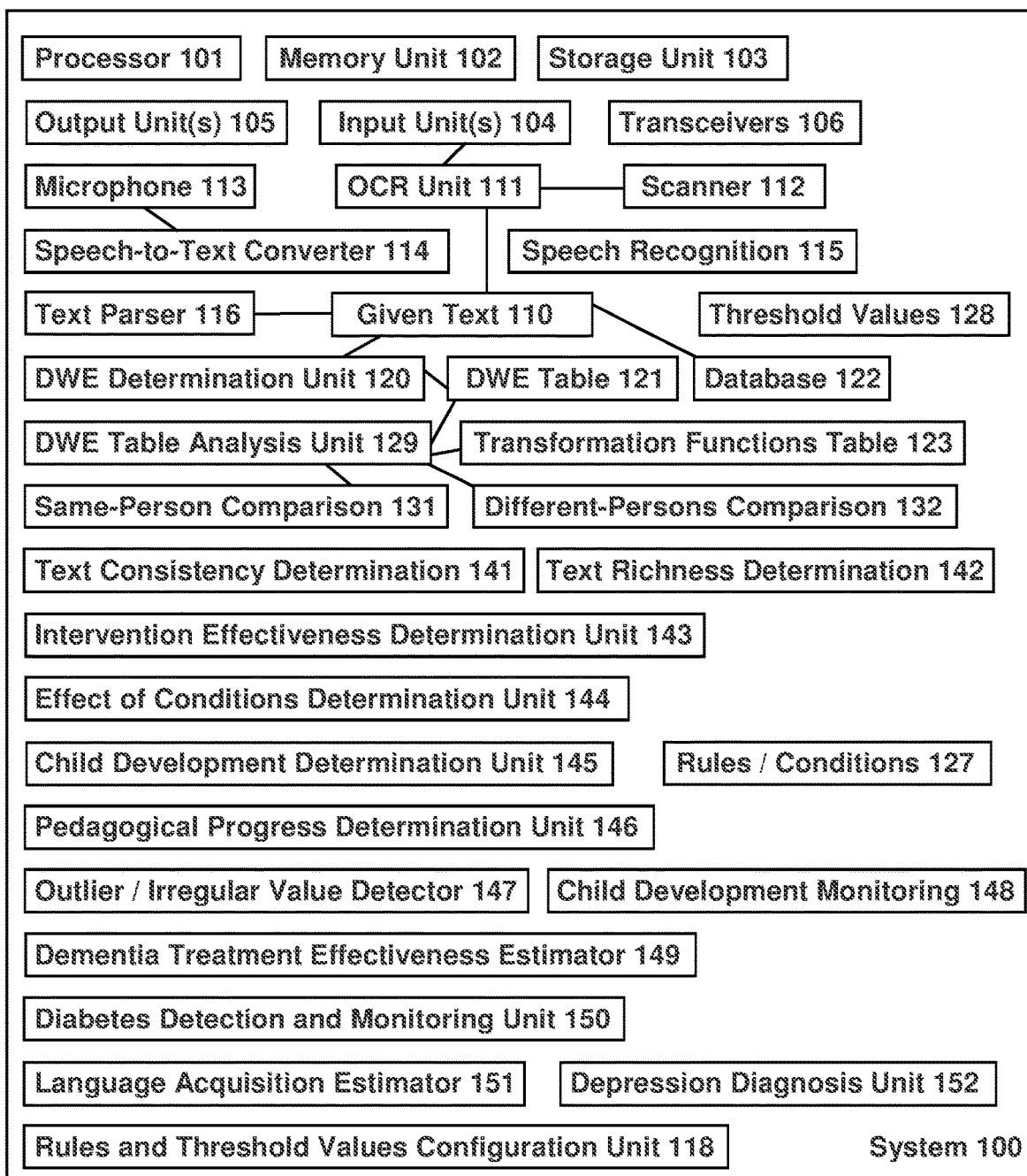
FIG. 1 is a schematic block-diagram illustration of a system, in accordance with some demonstrative embodiments of the present invention.

Reference is made to FIG. 1, which is a schematic block-diagram illustration of a system 100, in accordance with some embodiments of the present invention. System 100 may comprise, for example: a processor 101 (e.g., a Central Processing Unit (CPU), a Digital Signal Processor (DSP), a processing core, an Integrated Circuit (IC), and Application-Specific Integrated Circuit (ASIC), a controller, programmable controller); a memory unit 102 (e.g., Random Access Memory (RAM), Flash memory); a storage unit 103 (e.g., a hard disk drive (HDD), a solid state drive (SDD), an optical or electro-magnetic storage article or storage medium); one or more input units 104 (e.g., keyboard, mouse, touch-pad, touch-screen, multi-touch screen, microphone); one or more output units 105 (e.g., screen, touch-screen, monitor, display unit, audio speakers); one or more transceivers 106 (e.g., Wi-Fi transceiver; Bluetooth transceiver; cellular transceiver; 3G or 4G or 4G-LTE or 5G transceiver; wired transceiver; wireless transceiver); and other suitable hardware components and/or software components (e.g., power source; Operating System (OS); drivers; applications or "apps"; accelerometers; gyroscopes; compass units; device-orientation sensors; Global Positioning System (GPS) unit or location-finding unit; or the like).

In accordance with the present invention, a Given Text 110 is generated or produced or received, or is downloaded or fetched or copied from a remote server or from another device, or is uploaded or provided otherwise to the system. For example, a human user (e.g., a patient; or a person that is about to undergo a medical treatment or a therapy or other intervention) may type words using a physical keyboard, directly into the system 100, or indirectly onto another device which then transfers the typed text to the system 100 (e.g., via the transceiver(s) of system 100). Additionally or alternatively, the human user may hand-write the text onto a touch-screen with his finger or with a stylus; and an Optical Character Recognition (OCR) Unit 111 may convert the handwritten input into text. Additionally or alternatively, the human user may type the text onto a touch-screen using an on-screen keyboard which he taps with his fingers. Additionally or alternatively, a scanner 112 of system 100 may be used to scan a paper (or other tangible article) that has on it typed words and/or printed words and/or hand-written words, that were authored or written or types or printed by a human user; and the OCR Unit 111 may convert the scanned content into text, or may extract text from the scanned content. Additionally or alternatively, an audio microphone 113 may be used to capture or acquire speech of the user (e.g., words, utterances, or other audible content); and a Speech-to-Text Converter 114 or a Speech Recognition Unit 115 may then convert the captured audio into text, or may extract the text from the captured audio. Additionally or alternatively, the speech of the user may be received from another source, such as, may be received as a digital file or WAV file or MP3 file or AAC file, or may be received by requesting the user to telephone to a particular telephonic destination and to record his speech into a voice-mailbox that records his audio; and then, the Speech-to-Text Converter 114 or the Speech Recognition Unit 115 may convert the recorded or received audio into text, or may extract the text from the recorded or received audio.

In some embodiments, the Given Text 110 may comprise text portions that were intentionally and/or knowingly provided by a user; and/or may optionally comprise text portions that were captured without necessarily obtaining explicit knowledge or consent of the speaking person, or that were captured in a public setting, such as, capturing an audio speech of a public speaker who gives a lecture to an audience of 80 listeners; or for example, capturing an audio speech of some users in a medical clinical trial, without the users knowing whether they are part of a control group or they are part of treated persons; or capturing a text spoken or uttered by a person in a jurisdiction that legally allows one participant in a conversation to record an audio discussion without necessarily being obligated to notify to other participants that they are being recorded.

In some embodiments, Word Entropy (WE) of a given text may be defined or computed as follows: the given text has a total of N words; the given text has 11 unique words; for each unique word Wi in the given text, calculate relative frequency of this particular word in that given text, as follows:

$$p_i = \frac{n_i}{N},$$

i=1, ..., n; wherein ni is the number of times that this word appears in the given text. Then, Normalized Word Entropy (NWE) may be calculated, using the following equation, to yield a NWE value in the range of 0 to 1:

$$WE = \frac{-\sum_{i=1}^{n} p_i \cdot \log(p_i)}{\log(N)}$$

Rather than utilizing a conventional measurement of Word Entropy (WE) or Normalized Word Entropy (NWE), the present invention may define and utilize a unique new measurement of Dynamic Word Entropy (DWE); which may be defined, and may be calculated or computed by A DWE Determination Unit 120, as follows:

$$DWE_i = \frac{-\sum_{j=1}^{i} p_j \cdot \log(p_j)}{\log(i)}$$

In accordance with the DWE definition and function, for each word Wi in the given text, the DWE Determination Unit 120 computes is respective DWE value which is equal to the value of WE (or NWE) calculated for the text-portion that starts at the first word of the given text and that ends at the current word Wi (and includes the current word Wi).

In a demonstrative example, a given text (e.g., typed, or written, converted from speech, or obtained by other means as demonstrated above) includes 50 words. In a demonstrative implementation, DWE Determination Unit 120 calculates the DWE of the first 30 words; then calculates the DWE of the first 31 words; then calculate the DWE of the first 32 words; and so forth for 21 iterations, the last iteration calculating the DWE of the entire 50 words of the given text. In other implementations, the given text has N words; and the DWE Determination Unit 120 calculates the DWE of the first K words; then calculates the WE of the first K+1 words; then calculate the DWE of the first K+2 words; and so forth for (N−K+1) iterations, the last iteration calculating the DWE of the entire N words of the given text; wherein K<N. In some embodiments, the value of K may be configured as, for example, a hard-coded or fixed value (e.g., 25 or 30 or 35 or 40 or 45 words); or may be expressed as a percentage of N or as a fraction of N (for example, K is the closest integer to 10% of N; or, K is the closest integer to N/7); or may be expressed as a combination of such criteria (e.g., let K be the greater of: 32 or the closest integer to N/8).

The multiple values of DWE that are calculated by the DWE Determination Unit 120 for the Given Text 110, are stored in a DWE Table 121 that corresponds to this particular Given Text. Optionally, a Database 122 may store multiple records, wherein each record may comprise, for example, some or all of the following fields or data-items: (a) a copy of a particular Given Text, or a pointer or link or shortcut to a location that stores a copy of that particular Given Text; (b) an identifier or a unique identifier of the speaker or author of that particular Given Text (e.g., name; email address, identification number, or the like); (c) the length (e.g., the number of words) of the Given Text in words; (d) the number of unique words in that particular Given Text; (e) the value of K with regard to that particular Given Text; (f) the date and time, or date-stamp and time-stamp, in which the Given Text was captured or obtained or received; (g) an indication of whether the Given Text was sampled or captured Prior to an intervention, or During an intervention, or After an intervention; (h) the table of DWE values (or, an ordered list of the DWE values) that were computed for that Given Text.

The values of the DWE Table 121 may be analyzed or processed by a DWE Table Analysis Unit 129, which may also utilize one or more Transformation Functions described herein in conjunction with particular Threshold Values 128 and in conjunction with pre-defined Rules/Conditions 127, and may generate one or more Transformed Values described herein and/or may apply one or more rules or conditions or comparisons to threshold-values or threshold ranges, and may generate insights or indicators which quantify one or more characteristics of the Given Text and/or of the user who provided (spoke, authored, wrote, typed, dictated) the Given Text.

In a demonstrative example, a particular Given Text includes the following text-segment of 51 words: "Well, right now I just woke up from a mid-day nap. It's sort of weird, but ever since I moved to Texas, I have had problems concentrating on things. I remember starting my homework in 10th grade as soon as the clock struck 4 and not stopping until it was done."

The following table demonstrates the first eleven rows in the DWE Table 121 that were calculated in the first eleven iterations for that Given Text; in which N is 51, and K is set 30; and the first eleven iterations are:

| For the text portion until word number: | The DWE value is: |
|---|---|
| 30 | 0.946 |
| 31 | 0.948 |
| 32 | 0.95 |
| 33 | 0.952 |
| 34 | 0.954 |
| 35 | 0.955 |
| 36 | 0.957 |
| 37 | 0.958 |
| 38 | 0.96 |
| 39 | 0.961 |
| 40 | 0.953 |
| 41 | 0.954 |

For demonstrative purposes, only the first 11 iterations are shown; however, a full DWE table may be generated, stored, and utilized by system 100.

In accordance with the present invention, a Transformation Functions Table 123 may store representations of one or more functions or equations or formulas or transformation models. Each such Transformation Function may receive as input the list (or table) of DWE values that correspond to a particular given text that was spoken or written by a particular user; and may generate as output a Transformed Value which may be used to indicate a property or characteristic of the author or speaker, or of the text-producing abilities of that author or speaker. The Transformation Functions may be or may include, for example, average, mean, median, variance, standard deviation, range, maximum value, minimum value, or the like; and may be applied directly to the DWE values, or to differences or "deltas" between pairs of DWE values, or to other permutations or manipulations of the DWE values (e.g., their squared values, or their cubed values, or their square-root values, or the like).

The Applicants have realized that Transformed Values that are generated by such Transformation Function(s) based on the computed DWE values, may be utilized by system 100 as one or more quantitative measure(s) of factors related to speech of persons and/or related to the speaker or author himself, and/or may be utilized as an indicator to determine the success or failure or neutrality of a particular medical treatment or behavioral treatment or therapy or drug or other intervention; for example, by comparing the output value of the function when it processes a first text (e.g., generated by a patient before a medical treatment or other intervention) and processes a second text (e.g., generate by the same patient after a medical treatment or other intervention). For example, in order to determine the effectiveness or usefulness of a particular medical treatment or other intervention, the system may measure the difference between DWE of speech of a person before and after such treatment or intervention.

Additionally or alternatively, the calculation of the DWE values, and the calculation of the function output based on them, may provide other useful indications or quantitative measurements; for example, indicating speech consistency (or written text consistency) based on the standard deviation of differences between points of DWE (namely, $DWE_i$ for consecutive values of "i"); indicators of the level of education of the person; or the like. In a demonstrative example, the standard deviation of the DWE values of the given text shown above is approximately 0.05, which is a relatively high value (e.g., compared to a pre-defined threshold value), thereby enabling the system to indicate that the given text has reduced consistency and/or lacks consistency and/or that the speaker or author of the given text exhibits "jumps" from one topic to another.

In a first example, a Same-Person Comparison Unit 131 may operate to compare Transformed Values of two (or more) texts that were authored or spoken by the same person. In a demonstrative example, Adam typed a paragraph of 200 words (denoted as "Adam-Text-1") on April 1st; then, Adam underwent a particular treatment or therapy or received a particular drug on April 2nd; then, Adam types a different paragraph of 210 words (denoted as "Adam-Text-2") on April 3rd. The system 100 computes the DWE Table for Adam-Text-1 to generate a "Pre-Intervention-DWE-Table"; and computes separately the DWE Table for Adam-Text-2 to generate a "Post-Intervention-DWE-Table". A first particular Transformation Function (e.g., Standard Deviation) is applied, separately, to each one of these two DWE Tables of the two Given Texts of Adam; to generate, respectively, two Transformed Values. The Same-Person Comparison Unit 131 may then compare the two Transformed Values, based on one or more pre-defined criteria or condition or threshold values or ranges-of-values. For example, the first Transformed Value may indicate a pre-intervention standard deviation of 0.90, whereas the second Transformed Value may indicate a post-intervention standard deviation of 0.80; and the Same-Person Comparison Unit 131 may thus determine based on the decrease that the intervention was efficient and has increased the richness of texts generated by Adam; or conversely, may determine based on the decrease that the intervention was adverse and has reduced the richness of texts generated by Adam; or still conversely, may determine that the change in the Transformed Value from 0.90 to 0.80 is not sufficiently indicative of a significant effectiveness positively or negatively and that the intervention did not substantially affect the richness of texts generated by Adam.

In a second example of the Same-Person Comparison Unit 131, Adam typed a paragraph of 300 words (denoted as "Adam-Text-3") on May 1st; then, Adam underwent a particular treatment or therapy or received a particular drug on May 3rd; then, Adam types a different paragraph of 315 words (denoted as "Adam-Text-4") on May 6th. The system 100 computes the DWE Table for Adam-Text-3 to generate a "Pre-Intervention-DWE-Table"; and computes separately the DWE Table for Adam-Text-4 to generate a "Post-Intervention-DWE-Table". A second particular Transformation Function (e.g., Average) is applied, separately, to each one of these two DWE Tables of these two Given Texts of Adam; to generate, respectively, two Transformed Values. The Same-Person Comparison Unit 131 may then compare the two Transformed Values, based on one or more pre-defined criteria or condition or threshold values or ranges-of-values. For example, the first Transformed Value may indicate a pre-intervention average of 0.75, whereas the second Transformed Value may indicate a post-intervention average of 0.92; and the Same-Person Comparison Unit 131 may thus determine based on the increase that the intervention was efficient and has increased the richness of texts generated by Adam; or conversely, may determine based on the increase that the intervention was adverse and has reduced the richness of texts generated by Adam; or still conversely, may determine that the change in the Transformed Value from 0.75 to 0.92 is not sufficiently indicative of a significant effectiveness positively or negatively and that the intervention did not substantially affect the richness of texts generated by Adam.

In a third example of the Same-Person Comparison Unit 131, Adam undergoes a three-hour treatment on June 1st, starting at 8 AM and ending at 11 AM; for example, Adam is exposed to a particular gas-based medical substance that he inhales, or Adam receives a particular intravenous medicament continuously, or Adam takes a particular pill (or different pill) every 15 minutes during those three hours, or Adam undergoes a psychotherapy session or behavioral intervention session for three hours, or the like. During those three hours, Adam is requested to provide multiple different Given Texts; for example, to provide a fresh and original text of approximately 400 to 450 words long, every 30 minutes; totaling 7 different Given Texts for that 3-hour session of treatment or therapy. The system 100 computes the DWE Table for each one of those seven Given Texts, and generates seven respective DWE-Tables: the first one being a "pre-intervention" DWE table, the last one being a "post-intervention" DWE table, and the five other DWE tables in between them being "within-intervention" DWE tables. A particular Transformation Function (e.g., Median) is applied, separately, to each one of these seven DWE Tables of these seven Given Texts of Adam; to generate, respectively, seven Transformed Values. The Same-Person Comparison Unit 131 may then compare the seven Transformed Values, based on one or more pre-defined criteria or condition or threshold values or ranges-of-values; and may generate a graph or chart or other representation showing increase, decrease, or non-change in richness or consistency or other properties of the speech or text of Adam during the intervention time-period.

In a fourth example of the Same-Person Comparison Unit 131, Dan typed a paragraph of 350 words (denoted as "Dan-Text-1") on February 1st; and on the same day yet four hours later, Dan dictated or uttered a speech of 370 words which the system then converted into text (denoted as "Dan-Text-2"). The system 100 computes the DWE Table for Dan-Text-1 to generate a "Written-Text-DWE-Table"; and computes separately the DWE Table for Dan-Text-2 to generate a "Spoken-Text-DWE-Table" for the same user (Dan). A particular Transformation Function (e.g., Variance) is applied, separately, to each one of these two DWE Tables of these two Given Texts of Dan; to generate, respectively, two Transformed Values. The Same-Person Comparison Unit 131 may then compare the two Transformed Values, based on one or more pre-defined criteria or condition or threshold values or ranges-of-values. For example, the first Transformed Value may indicate a Written Text variance of 2.4, whereas the second Transformed Value may indicate a Spoken Text variance of 2.7; and the Same-Person Comparison Unit 131 may thus determine based on the difference that the written text of Dan has greater richness or consistency than the spoken text of Dan; or conversely, that the written text of Dan has smaller richness or consistency than the spoken text of Dan; or yet conversely, that the difference is not sufficiently significant and that the written text and spoken text of Dan have generally similar or almost identical levels of richness of consistency.

In a fifth example, a Different-Persons Comparison Unit 132 may operate to compare Transformed Values of two (or more) texts that were authored or spoken, respectively, by two (or more) different persons. In a demonstrative example, Bob typed a paragraph of 330 words (denoted as "Bob-Text-1") on July 1st; and Cathy typed a different paragraph of 340 words (denoted as "Cathy-Text-1") on July 5th. The system 100 computes the DWE Table for Bob-Text-1 to generate a first DWE-Table; and computes separately the DWE Table for Cathy-Text-1 to generate a second DWE-Table. A particular Transformation Function (e.g., Maximum Value) is applied, separately, to each one of these two DWE Tables of the two Given Texts of Bob and Cathy; to generate, respectively, two Transformed Values. The Different-Persons Comparison Unit 132 may then compare the two Transformed Values, based on one or more pre-defined criteria or condition or threshold values or ranges-of-values. For example, the Transformed Value of Bob may be 0.68, whereas the Transformed Value of Cathy may be 0.84; and the Different-Persons Comparison Unit 132 may thus determine based on the difference that the text richness or consistency of Bob is greater than that of Cathy; or conversely, that the text richness or consistency of Bob is smaller than that of Cathy; or still conversely, that the difference in the Transformed Values (0.68 versus 0.84) is not sufficiently indicative of a significant difference in those (or other) parameters with regard to Bob relative to Cathy (or vice versa).

In some embodiments, two or more different Transformation Functions may operate on the DWE Tables, and two or more different Transformation Values may be used in order to reach a determination with regard to the same person and/or with regard to multiple persons. For example, if the Standard Deviation values of the two DWE tables is greater than X, and the Median values of the two DWE tables is smaller than Y, then, the system may determine that the first DWE table reflects a given text that has greater consistency, or greater richness, or other property, relative to the given text of the second DWE table.

In some embodiments, the conditions or threshold values or threshold ranges-of-values or the rules for comparing Transformed Values, and/or the particular Transformation Functions to be utilized, may be pre-defined or pre-configured or may be hard-coded. In other embodiments, they may be dynamically modified or determined, by taking into account one or more other parameters which may be known about the particular user, such as the user's gender, age, age-range, profession, or the like. For example, the system may utilize a first set of threshold values and/or a first set of transformation functions in order to assess the richness or consistency (or other characteristics) of texts that are authored or by 7-year-old children, and may utilize a second, different, set of threshold values and/or a second, different, set of transformation functions in order to assess the richness or consistency (or other characteristics) of texts that are authored by 35-year old adults. In another example, the system may utilize a first set of threshold values and/or a first set of transformation functions in order to assess the richness or consistency (or other characteristics) of texts that are spoken by males in the age-range of 30 to 35 year old, and may utilize a second, different, set of threshold values and/or a second, different, set of transformation functions in order to assess the richness or consistency (or other characteristics) of texts that are spoken by females in that same age-range. In another example, the system may utilize a first set of threshold values and/or a first set of transformation functions in order to assess the richness or consistency (or other characteristics) of texts that are dictated by adult users who are physicians; and may utilize a second, different, set of threshold values and/or a second, different, set of transformation functions in order to assess the richness or consistency (or other characteristics) of texts that are dictated by adult users who are attorneys.

In another example, given texts that span different length (in words, and/or in characters), or that include a different number of unique words, may be subject to different threshold values and/or transformation function(s) for their analysis; for example, such that given texts having a length in the range of 300 to 399 words (or having this range of unique words) may be subject to analysis using a first set of transformation function(s) and/or a first set of threshold values; whereas, given texts having a length in the range of 400 to 499 words (or having this range of unique words) may be subject to analysis using a second, different, set of transformation function(s) and/or a second, different, set of threshold values. In some embodiments, multiple such factors or user-characteristics may be utilized in combination or in the aggregate.

The above-mentioned comparisons and analysis operations may optionally be carried out by one or more dedicated units or modules of system 100; for example, a Text Consistency Determination Unit 141 may generate (based on the computed Transformed Values) a text consistency score or indicator which quantifies the level of consistency (or inconsistency) of a given text; a Text Richness Determination Unit 142 may generate (based on the Transformed Values) a text richness score or indicator which quantifies the level of richness (or dullness) of a text. Additionally or alternatively, an Intervention Effectiveness Determination Unit 143 may generated, based on the Transformed Values, a score or indicator which quantifies or indicates whether a particular intervention was effective or non-effective, or whether a particular intervention caused improvement or regression or non-change, or the like.

In some embodiments, system 100 may be used in conjunction with healthcare applications or healthcare-related goals or objectives; for example, to estimate or determine or quantify the effectiveness and/or efficiency and/or efficacy and/or usefulness of a particular drug or medicament or therapy or medical procedure or medical treatment or other treatment or therapy, or physical therapy or speech therapy or psychological therapy or psychotherapy sessions.

In some embodiments, the system may determine or estimate the change in cognitive ability and/or cognitive impairment; for example, of patients having dementia or Alzheimer or other conditions, medical conditions, mental conditions, physical conditions, or the like. For example, a change in the value(s) of DWE and/or in the Standard Deviation of the DWE table of a patient, may be used by the system to reach a determination that a particular treatment was effective and/or helpful. In some embodiments, for example, a standard deviation value of a DWE table, which is greater than a pre-defined threshold value, may be used by the system to determine change(s) of topics during text generation (writing or speech), and/or to further determine that the author or speaker may have disconnected thoughts which may result from mental-health problems. In some embodiments, the system may determine or estimate the change in physical ability and/or physical impairment and/or physical conditions; for example, of patients having diabetes; or to estimate and to provide quantitative measures with regard to the effects of one or more conditions or adverse conditions or positive conditions (e.g., sleep deprivation, hunger, thirst, stress; or on the contrary, being well-fed and well-rested) affect mental abilities and/or speech and language generation of person(s). In some embodiments, the system may further analyze data in order to determine what type(s) of physical and/or psychological profile(s) are the most resistant (or the least resistant) to adverse conditions (or conversely, to positive conditions); for example, to determine that diabetic males in the age-range of 35 to 45 years old who suffer from hunger and sleep deprivation, are more susceptible to reduction in their speech richness and/or consistency relative to diabetic females in the same age-range who suffer from the same two conditions. The system may further be used as a research tool, to generate new insights with regard to these and/or other conditions and their effects or results. Such analysis and generation of insights may be performed, for example, by an Effect of Conditions Determination Unit 144; which may be fed data about the conditions that are tested and the characteristics of the users involved (e.g., gender, race, age, age-range, profession, or the like); and it then proceeds to analyze the DWE of those users and Transformed Values that were derived from such DWE values or DWE tables.

System 100 may further be used, additionally or alternatively, in a childcare setting or for educational or pedagogical purposes or for monitoring the development of an infant or toddler or child or a minor. Such analysis and generation of insights may be performed by a Child Development Determination Unit 145 and/or by a Pedagogical Progress Determination Unit 146. For example, a group of children of the same age or age range and/or the same gender (e.g., males in the age range of 48 to 49 months old), may be requested to tell or dictate a story of approximately 250 words about their day at a childcare facility or about their weekend adventures; and a DWE table may be generated by the system. A Transformed Value may be computed for each one of the DWE tables, using the same Transformation Function. The list of Transformed Values may then be processed by the systems, and outliers or abnormal or irregular values may be detected, indicating an abnormal or irregular or delayed speech development or language development. For example, each child in a group of 10 children may provide his text for analysis; the system may detect that the Transformed Value of each child (that is based on the same Transformation Function that was applied to the DWE table of each child) is in the range of 0.90 to 0.93, except for one of these children whose Transformed Value is 0.71; this irregular value may be used by the system to determine, and to generate a notification, that this particular child may have a developmental delay, or conversely, that this particular child may be gifted and talented (e.g., based on the particular Transformation Function that was used). The system may thus compare absolute values of DWE values and/or DWE tables and/or Transformed Values of such DWE tables, at a fixed point or age, in order to reveal particular children that have difficulties in acquiring language or, conversely, the system may generate an insight that they are advanced or gifted or irregularly talented; thereby providing quantitative measurement of speech and language acquisition.

Some embodiments of the present invention may thus operate to monitor, diagnose and/or estimate the development of infants, toddlers, children, teenagers, minors, and/or students or pupils (e.g., particularly in kindergarten and elementary school, or even in middle school and high school). Comparison of absolute values of DWE at fixed time-points or age intervals may enable the system to detect children that have difficulties in acquiring language and/or processing language and/or utilizing language correctly to express ideas and/or processing. The DWE analysis of the present invention may provide a quantitative measure of language acquisition, and/or may be an invaluable tool for speech-language pathologists working with children or minors that were diagnosed with (or are suspected to have) developmental delays and/or medical disorders.

In a related implementation, the DWE analysis of the present invention may measure and compare language richness of students or pupils in different schools or classes or groups or study-courses, thereby monitoring the contribution of a school (or a teacher, or a department, or an educational system, or a pedagogical approach, or a teaching/learning tool) to students' development (e.g., optionally utilizing comparisons with control groups). This method may also be used to monitor and/or detect the progress of individual students, and/or to detect a student having slow or slower or slower-than-average or slower-than-others progress (e.g., in suspected developmentally challenged students), and/or to detect rapid or faster progress in children that are advanced or gifted or talented.

In some embodiments, a Language Acquisition Estimator 151 may operate to perform the above-mentioned estimations or determinations or detections, based on DWE analysis. In some embodiments, the Language Acquisition Estimator 151 also operate to monitor the linguistic development or progress of children or minors in multilingual families, whose language development is different from those of children in monolingual families. Optionally, the Language Acquisition Estimator 151 may perform the DWE analysis of the present invention in order to monitor, estimate and/or characterize the progress of acquisition of a secondary language or a second language, or acquisition of a language that is not the person's mother-tongue. For example, an adult who was born and raised in France and speaks only French, may relocate to the United States and may gradually learn English as a second language; and the Language Acquisition Estimator 151 may periodically (e.g., daily, weekly, monthly) perform DWE analysis of texts that are spoken and/or written by that person, in order to estimate or monitor or determine the progress of English language acquisition by that person.

Optionally, an Outlier/Irregular Value Detector 147 may operate to classify or to cluster or to group together DWE values or their respective Transformed Values, and to detect outlier values or irregular or abnormal values which may, in turn, indicate an irregular development (e.g., speech and language development; mental development; or the like) of the respective child or person. In some embodiments, optionally, a Child Development Monitoring Unit 148 may be responsible for collecting Given Texts of children or minors at certain particular time-points or age points (e.g., at age 4 years, at age 5 years, at age 6 years, and so forth); to run DWE analysis and Transformed Values analysis as described; and to detect outliers or abnormal or irregular values which point to child development problems or delays, or conversely may point to advanced or hastened development in some cases (e.g., depending on the Transformation Function(s) being used and/or the threshold values being used).

In some embodiments, based on comparison of DWE values (or their Transformed Values) to threshold values or ranges that characterize neuro-typical children of the general population, the Child Development Monitoring Unit 148 may generate notification or warnings or estimates that a particular child may have one or more conditions, for example, Autistic Spectrum Disorder (ASD), or Asperger's syndrome, or Language/Auditory/Speech processing disorder, or Attention-Deficit/Hyperactivity Disorder (ADHD), or the like. In some embodiments, such determination may be based, in whole or in part, additionally or alternatively, on comparison of DWE values (or their Transformed Values) to values that characterize children (or persons) have such conditions, rather than (or in addition to) comparing them to corresponding values of neuro-typical children (or persons).

The system may similarly be used to monitor, assess, estimate and/or determine a level of development of pupils or students in school or in an educational facility or childcare facility. For example, the DWE values and their Transformation Values may provide measures or level or indicators of language richness of students in different schools or in the same school, or in different classes or in the same class; and/or may enable monitoring of the contribution of a particular school (or teacher, or topic learned, or pedagogical method, or educational method, or an educational tool such as computer-based learning) to student's development, optionally by utilizing comparisons to control group(s) (e.g., students who used a particular pedagogical approach or educational tool, compared versus students who did not use that particular pedagogical approach or that educational tool).

In some embodiments, a Dementia Treatment Effectiveness Estimator 149 may operate to determine or estimate the effectiveness or usefulness of medical treatment(s) or other interventions with regard to a person having Dementia. The Applicants have realized that different kinds of dementia may primarily impact language, such as progressive non-fluent aphasia (PNFA) or temporal variant of frontotemporal dementia (TV-FTD, or semantic dementia), which adversely affect speech production and/or may cause the loss of nuance or meaning in terms. In some implementations, certain particular changes in the values of DWE for a given person, and/or the standard deviation of the DWE thereof, may indicate effectiveness of the treatment or intervention. In some implementations, significant changes in the standard deviation may indicate that a change in topics while speaking or writing texts might be linked to disconnected thoughts, and/or to an increasing inability to produce more advanced vocabulary, and/or to a compounding incapacity to recognize the significance of objects, resulting from dementia or a dementia-related psychological condition.

In some embodiments, a Diabetes Detection and Monitoring Unit 150 may operate to monitor and/or detect and/or diagnose and/or characterize diabetes patients or persons who are suspected to be or possibly are diabetic or are candidates for diabetes diagnosis. Such diabetic patients or persons may experience hypoglycemia, which in turn may cause (or may deteriorate already-existing) language difficulties and/or slur of speech. For example, type-1 diabetes hypoglycemia may negatively affect or adversely impact on reading span and/or subject-verb agreement. The DWE analysis of the present invention may provide a quantitative measure of how severe these negative effects are on diabetes patients, and/or may enable the system to measure linguistic improvement as an indicator of positive responses to treatment.

In some embodiments, a Depression Diagnosis Unit 152 may operate to diagnose or estimate clinical depression, its existence and/or its level of severity or intensity, based on DWE analysis of persons(s) that are suspected or are known to have clinical depression. The Applicants have realized that language patterns in mildly depressed or clinically depressed individuals may be measurably different from persons experiencing temporary episodes of sadness or persons in euthymic or neutral states. For example, depressed persons may use more descriptive language instead of analytical, single-clause sentences, and/or may put an emphasis on the past (e.g., may more frequently use the past tense); and DWE analysis by the system of the present invention may flag such speech and language characteristics which, in turn, may enable diagnosis or estimation of mild depression or clinical depression. Additionally or alternatively, DWE analysis may measure the restoration of speech patterns in non-depressed persons as an indicator of treatment's effectiveness or usefulness or success. For example, the Depression Diagnosis Unit 152 may search for increased frequency of analytical language, and/or multi-clause sentence structure, and/or appearance of imperfect (present and future) tenses. Additionally or alternatively, a similar unit or module may operate to utilize DWE analysis in order to estimate or detect anxiety, suicidal intentions, or other conditions.

In some embodiments, the DWE analysis may be performed after a text parsing or text preparation process, performed by a Text Parser 116 on a received (or generated) text in order to prepare it for the DWE analysis. For example, the original text may be "cleaned" by the Text Parser 116, by removing excessive spaces (e.g., replacing two (or more) consecutive spaces with a single space), and/or by correcting typographical errors via a spell-checker module (e.g., changing "receieved" to "received"), and/or by preparing or extracting a list of words (e.g., a word may be identified as a string of characters between two non-consecutive "Space" characters), or the like. Such parsing or preparation may, in some embodiments, improve the accuracy of the DWE analysis. In some embodiments, the Text Parser 116 may also be responsible for performing other preparation operations towards DWE analysis; for example, calculating the number of words in a text, preparing the words as discrete word units or word elements, tracking and counting unique words in the text, or the like.

It would be appreciated that the present invention may be exercised based on the textual description above and herein, and/or based on the accompanying drawings, and optionally by utilizing programming and development by a person of ordinary skilled in the art in view of the teachings of this patent applications; specifically, which Transformation Function(s) to utilize, and/or which Threshold Value(s) or threshold ranges-of-values to utilize, in order to detect a particular condition or in order to determine effectiveness (positive or negative) or ineffectiveness of an intervention, may be selected and/or fine-tuned to accommodate a particular implementation and its goals; for example, based on data that is analyzed with regard to Given Texts that are known to have richness or dullness, or with regard to Given Texts that are known to be generated by persons having a particular medical condition or mental condition.

In a first example of how the present application enables the exercise of the present invention, a first developer may wish to implement an embodiment of the present invention in order to provide a machine-based system that determines whether a person has dementia. The developer may approach a group of 30 persons that are known to have dementia (e.g., based on medical diagnosis done by human physicians in accordance with the prevailing medical standards), and may obtain from them 30 texts, each text being approximately 260 to 290 words long. Then, the developer may approach a group of 30 other persons that are known to not have dementia (e.g., as determined by human physicians in accordance with the prevailing medical standards), and may obtain from them 30 other texts, each text being approximately 260 to 290 words long. Then, the developer may instruct the system to generate DWE tables for each one of the 30 texts from the persons having dementia; and may instruct the system to generate DWE tables for each one of the other 30 texts from the persons that do not have dementia. Then, the developer may instruct the system to generate separately, for each one of the sixty DWE tables, an Average value, and a Median value, and a Standard Deviation value; thereby obtaining three sets of 60 such values. Each set of 60 values may be fed into a clustering or grouping algorithm, or may even be fed into an Excel sheet or may be reviewed manually, in order to detect clear clusters or ranges of values that correspond to each group of users. For example, it may be observed by the developer, manually or by using a data clustering tool, that each one of the thirty DWE tables of the 30 persons having dementia, has a Standard Deviation in the range of 0.91 to 0.95; whereas, each one of the thirty DWE tables of the 30 persons that do not have dementia, has a Standard Deviation in the range of 0.65 to 0.69. Additionally, it may be observed by the developer, manually or by using a data clustering tool, that each one of the thirty DWE tables of the 30 persons having dementia, has a Median value in the range of 0.82 to 0.88; whereas, each one of the thirty DWE tables of the 30 persons that do not have dementia, has a Median value in the range of 0.81 to 0.89. Accordingly, it may be concluded, firstly, that the Median function is not a suitable (or useful) Transformation Function for diagnosing or monitoring persons with regard to dementia (although the Median value may be useful or suitable for other diagnosis purposes or for other monitoring purposes). Secondly, it may be concluded that the Standard Deviation function is a suitable (or useful) Transformation Function for diagnosing or monitoring persons with regard to dementia. Thirdly, it may be concluded that the system may be configured to utilize particular rules or threshold values with regard to diagnosing or monitoring dementia; for example, a rule of "if the Standard Deviation of the DWE table is smaller than 0.70, then determine that the person does not have dementia", or a rule of "if the Standard Deviation of the DWE table is greater than 0.90, then determine that the person has dementia". Fourthly, it may be concluded which rules or threshold values to utilize in order to detect or to determine positive progress or improvement, or in order to determine negative progress or regression, or in order to determine non-change or non-progress; for example, a first rule that a decrease of at least 0.02 in the value of Standard Deviation of the DWE table for the same person (e.g., post-intervention, compared to pre-intervention), may indicate that the intervention was effective in reducing dementia; and/or, a second rule that an increase of at least 0.03 in the value of Standard Deviation of the DWE table of the same person (e.g., post-intervention, compared to pre-intervention), may indicate that the intervention has actually increased the person's dementia; and/or, a third rule that a change (either an increase or a decrease) of under 0.02 in the value of Standard Deviation of DWE table of the same person (e.g., post-intervention, compared to pre-intervention), may indicate that the intervention did not affect the dementia condition, neither positively nor negatively. Accordingly, the present invention may be implemented by carrying out, initially, such preliminary analysis, thereby enabling to configure the determination rules and/or the threshold values and/or the transformation functions that would actually be utilized by the system in order to achieve a particular diagnosis goal or monitoring goal. These operations may be performed by, or may be assisted by, a Data Clustering Unit 117; and the configuration or definition of rules, as well as which Transformation Functions to utilize and which Threshold Values (or ranges) to utilize, may be implemented via a Rules and Threshold Values Configuration Unit 118, which in some embodiments may operate automatically or semi-automatically by identifying clusters or groups of data-points that correspond to DWE tables of persons that are known to have (or, not to have) a particular condition or characteristic; thereby enabling the system and its Rules and Threshold Values Configuration Unit 118 to automatically and/or autonomously perform self-learning and to configure or set its own rules and threshold values.

In a second example of how the present application enables the exercise of the present invention, a second developer may wish to implement an embodiment of the present invention in order to provide a machine-based system that determines whether or not a six-year-old child has speech and language delays. The developer may approach a group of 40 six-year-old children that are known to have speech and language delays (e.g., based on medical diagnosis done by human physicians or human Speech Language Pathologists in accordance with the prevailing medical standards), and may obtain from them 40 texts, each text being approximately 210 to 240 words long. Then, the developer may approach a group of 40 other six-year-old children that are known to not have speech and language delays (e.g., as determined by human physicians or human Speech Language Pathologists in in accordance with the prevailing medical standards), and may obtain from them 40 other texts, each text being approximately 210 to 240 words long. Then, the developer may instruct the system to generate DWE tables for each one of the 40 texts from the children having speech and language delays; and may instruct the system to generate DWE tables for each one of the other 40 texts from the children that do not have speech and language delays. Then, the developer may instruct the system to generate separately, for each one of the eighty DWE tables, an Average value, and a Median value, and a Standard Deviation value; thereby obtaining three sets of 80 such values. Each set of 80 values may be fed into a clustering or grouping algorithm, or may be fed into an Excel sheet or may be reviewed manually, in order to detect clear clusters or ranges of values that correspond to each group of users.

For example, it may be observed by the developer, manually or by using a data clustering tool, that each one of the forty DWE tables of the 40 children having speech and language delays, has a Standard Deviation in the range of 0.42 to 0.48; whereas, each one of the forty DWE tables of the 40 children that do not have speech and language delays, has a Standard Deviation in the range of 0.88 to 0.92. Additionally, it may be observed by the developer, manually or by using a data clustering tool, that each one of the forty DWE tables of the 40 children having speech and language delays, has an Average value in the range of 0.67 to 0.72; whereas, each one of the forty DWE tables of the 40 children that do not have speech and language delays, has an Average value in the range of 0.68 to 0.73.

Accordingly, it may be concluded, firstly, that the Average function is not a suitable (or useful) Transformation Function for diagnosing or monitoring six-year-old children with regard to speech and language delays (although the Average value may be useful or suitable for other diagnosis purposes or for other monitoring purposes). Secondly, it may be concluded that the Standard Deviation function is a suitable (or useful) Transformation Function for diagnosing or monitoring six-year-old children with regard to speech and language delays. Thirdly, it may be concluded that the system may be configured to utilize particular rules or threshold values with regard to diagnosing or monitoring speech and language delays for six-year-old children; for example, a rule of "if the Standard Deviation of the DWE table is equal to or greater than 0.88, then determine that the child does not have speech and language delays", or a rule of "if the Standard Deviation of the DWE table is equal to or smaller than 0.72, then determine that the child has speech and language delays". Fourthly, it may be concluded which rules or threshold values to utilize in order to detect or to determine positive progress or improvement, or in order to determine negative progress or regression, or in order to determine non-change or non-progress; for example, a first rule that an increase of at least 0.02 in the value of Standard Deviation of the DWE table the same child (e.g., post-intervention, compared to pre-intervention), may indicate that the intervention was effective in reducing speech and language delays; and/or, a second rule that a decrease of at least 0.03 in the value of Standard Deviation of the DWE table of the same child (e.g., post-intervention, compared to pre-intervention), may indicate that the intervention has actually increased the child's speech and language delays; and/or, a third rule that a change (either an increase or a decrease) of under 0.02 in the value of Standard Deviation of DWE table of the same child (e.g., post-intervention, compared to pre-intervention), may indicate that the intervention did not affect the speech and language delays, neither positively nor negatively.

In some embodiments, optionally, the DWE analysis of the present invention may be utilized in conjunction with text that is generated by a machine or a computer or by an Artificial Intelligence (AI) unit or by a Machine Learning (ML) unit, in order to assess and/or measure the richness and/or consistency and/or quality and/or other characteristics of such machine-generated text(s). For example, a first AI-based machine may generate a first text of approximately 250 words regarding a particular topic by using a first AI or ML algorithm; and separately, a second AI-based machine may generate a second, different, text of approximately 250 words regarding the same particular topic (or regarding a different topic) by busing a second, different, AI or ML algorithm. The system of the present invention may perform DWE analysis, separately, on each one of these two machine-generated texts, in order to quantify or characterize the richness and/or the consistency of those texts; and the DWE analysis results may be used by the system of the present invention in order to rank or score the quality of the corresponding text-generating algorithms. For example, in a demonstrative implementation, if the first machine-generated text yields a first DWE table having a Standard Deviation of 0.90 and a Median of 0.75, whereas the second machine-generated text yields a second DWE table having a Standard Deviation of 0.60 and a Median of 0.55, then the system may determine that the text-generating algorithm (or machine) that generated the first text is superior or is better relative to the second text-generating algorithm (or machine).

Figure 2:
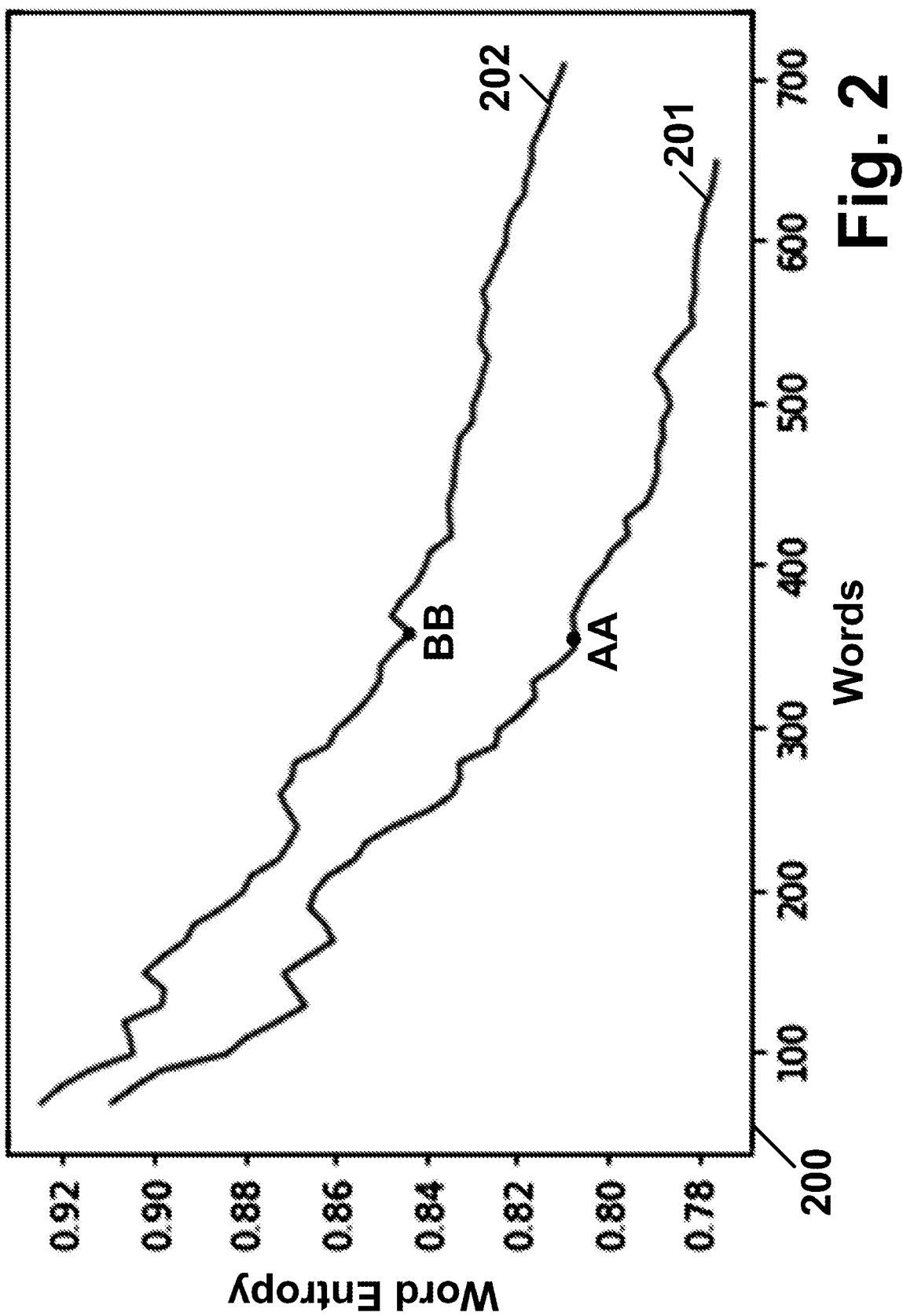
FIG. 2 is a schematic illustration of a chart demonstrating pre-intervention and post-intervention Dynamic Word Entropy (DWE), in accordance with some demonstrative embodiments of the present invention.

Reference is made to FIG. 2, which is a schematic illustration of a chart 200 demonstrating DWE values of two given texts of the same person, in accordance with some demonstrative embodiments of the present invention. Line 201 indicates DWE values of a pre-intervention text of approximately 650 words; and line 202 indicates DWE values of a post-intervention text of approximately 710 words. The horizontal axis indicates the number of words in the given text. The vertical axis indicates the DWE value. Point AA indicates, for example, that the DWE value of the first 350 words of the pre-intervention text, is approximately 0.81. Point BB indicates, for example, that the DWE value of the first 350 words of the post-intervention text, is approximately 0.85. The chart 200 demonstrates that the pattern of DWE values of a person, and/or the changes in DWE values of a person, may be utilized to monitor, estimate and/or determine the effect of an intervention. Other suitable charts of graphs may be used or may be generated, in accordance with embodiments of the present invention.

Some embodiments of the present invention include a method comprising: (a) obtaining a text of a user; (b) determining that the text comprises N words; (c) determining an integer K that is smaller than N; (d) generating a Dynamic Word Entropy (DWE) table of said text, wherein the DWE table comprises 1+N−K rows, wherein each row in the DWE table has a row-number denoted R, wherein each row in the DWE table comprises: a Word Entropy value determined for a text-segment of said text which consists of the first K+R−1 words of said text; (e) based on analysis of the DWE table, generating an output which quantifies a characteristic of said user.

In some embodiments, step (e) comprises: applying a particular Transformation Function to said DWE table, and generating a Transformed Value corresponding to said DWE table; based on said Transformed Value generated from said DWE table, generating the output which quantifies said characteristic of said user.

In some embodiments, step (e) comprises: applying a particular Transformation Function to said DWE table, and generating a Transformed Value corresponding to said DWE table; wherein the Transformation Function comprises a function selected from the group consisting of: average, median, variance, standard deviation; based on said Transformed Value generated from said DWE table, generating the output which quantifies said characteristic of said user.

In some embodiments, step (e) comprises: applying a particular Transformation Function to said DWE table, and generating a Transformed Value corresponding to said DWE table; based on said Transformed Value generated from said DWE table, generating output which quantifies richness of speech of said user.

In some embodiments, step (e) comprises: applying a particular Transformation Function to said DWE table, and generating a Transformed Value corresponding to said DWE table; based on said Transformed Value generated from said DWE table, generating output which quantifies consistency of speech of said user.

In some embodiments, step (e) comprises: applying a particular Transformation Function to said DWE table, and generating a Transformed Value corresponding to said DWE table; based on a comparison between (i) said Transformation Value corresponding to said DWE table, and (ii) a pre-defined threshold value that is associated with a particular medical condition, determining whether said user has or does not have said particular medical condition.

In some embodiments, step (e) comprises: applying a particular Transformation Function to said DWE table, and generating a Transformed Value corresponding to said DWE table; based on a comparison between (i) said Transformation Value corresponding to said DWE table, and (ii) a pre-defined threshold value that is associated with persons having dementia, determining whether said user has or does not have dementia.

In some embodiments, step (e) comprises: applying a particular Transformation Function to said DWE table, and generating a Transformed Value corresponding to said DWE table; based on a comparison between (i) said Transformation Value corresponding to said DWE table, and (ii) a pre-defined threshold value that is associated with persons having diabetic hypoglycemia, determining whether said user has or does not have diabetic hypoglycemia.

In some embodiments, step (e) comprises: applying a particular Transformation Function to said DWE table, and generating a Transformed Value corresponding to said DWE table; based on a comparison between (i) said Transformation Value corresponding to said DWE table, and (ii) a pre-defined threshold value that is associated with persons having clinical depression, determining whether said user has or does not have clinical depression.

In some embodiments, step (e) comprises: applying a particular Transformation Function to said DWE table, and generating a Transformed Value corresponding to said DWE table; based on a comparison between (i) said Transformation Value corresponding to said DWE table, and (ii) a pre-defined threshold value that is associated with persons having suicidal intent, determining whether said user has or does not have suicidal intent.

In some embodiments, step (e) comprises: applying a particular Transformation Function to said DWE table, and generating a Transformed Value corresponding to said DWE table; based on a comparison between (i) said Transformation Value corresponding to said DWE table, and (ii) a pre-defined threshold value that is associated with persons having speech and language delays, determining whether said user has or does not have speech and language delays.

In some embodiments, said text is a pre-intervention text of said user; wherein said DWE table is a pre-intervention DWE table; wherein step (e) comprises: applying a particular Transformation Function to said DWE table, and generating a pre-intervention Transformed Value corresponding to said DWE table; wherein the method further comprises: obtaining a second text which is a post-intervention text of said user; performing the operations of steps (b) through (d) with regard to said post-intervention text of said user, and generating a post-intervention DWE table corresponding to said post-intervention text of said user; based on an analysis of both (i) the pre-intervention DWE table and (ii) the post-intervention DWE table, determining whether or not said intervention has affected said user.

In some embodiments, said text is a pre-intervention text of said user; wherein said DWE table is a pre-intervention DWE table; wherein step (e) comprises: applying a particular Transformation Function to said DWE table, and generating a pre-intervention Transformed Value corresponding to said DWE table; wherein the method further comprises: obtaining a second text which is a post-intervention text of said user; performing the operations of steps (b) through (d) with regard to said post-intervention text of said user, and generating a post-intervention DWE table corresponding to said post-intervention text of said user; based on an analysis of both (i) the pre-intervention DWE table and (ii) the post-intervention DWE table, generating an indicator that quantifies an effect of said intervention on said user.

In some embodiments, said text is a pre-intervention text of said user; wherein said DWE table is a pre-intervention DWE table; wherein step (e) comprises: applying a particular Transformation Function to said DWE table, and generating a pre-intervention Transformed Value corresponding to said DWE table; wherein the method further comprises: obtaining a second text which is a post-intervention text of said user; performing the operations of steps (b) through (d) with regard to said post-intervention text of said user, and generating a post-intervention DWE table corresponding to said post-intervention text of said user; applying a particular Transformation Function to the pre-intervention DWE table, and generating a pre-intervention Transformed Value corresponding to said pre-intervention DWE table; applying said particular Transformation Function to the post-intervention DWE table, and generating a post-intervention Transformed Value corresponding to said post-intervention DWE table; based on a comparison between (i) the pre-intervention Transformed Value and (ii) the post-intervention Transformed Value, determining whether or not said intervention has affected said user.

In some embodiments, said text is a pre-intervention text of said user; wherein said DWE table is a pre-intervention DWE table; wherein step (e) comprises: applying a particular Transformation Function to said DWE table, and generating a pre-intervention Transformed Value corresponding to said DWE table; wherein the method further comprises: obtaining a second text which is a post-intervention text of said user; performing the operations of steps (b) through (d) with regard to said post-intervention text of said user, and generating a post-intervention DWE table corresponding to said post-intervention text of said user; applying a particular Transformation Function to the pre-intervention DWE table, and generating a pre-intervention Transformed Value corresponding to said pre-intervention DWE table; applying said particular Transformation Function to the post-intervention DWE table, and generating a post-intervention Transformed Value corresponding to said post-intervention DWE table; based on a comparison between (i) the pre-intervention Transformed Value and (ii) the post-intervention Transformed Value, generating an indicator that quantifies an effect of said intervention on said user.

In some embodiments, step (e) comprises: applying a first particular Transformation Function to said DWE table, and generating a first Transformed Value corresponding to said DWE table; applying a second particular Transformation Function to said DWE table, and generating a second Transformed Value corresponding to said DWE table; applying a multiple-parameter analysis, by checking whether the first Transformed Value is within a first range-of-values, and by checking whether the second Transformed Value is within a second range-of-vales; based on results of the multiple-parameter analysis, determining whether said user has or does not have a particular medical condition.

In some embodiments, step (e) comprises: applying a first particular Transformation Function to said DWE table, and generating a first Transformed Value corresponding to said DWE table; applying a second particular Transformation Function to said DWE table, and generating a second Transformed Value corresponding to said DWE table; applying a multiple-parameter analysis, by checking whether the first Transformed Value is within a first range-of-values, and by checking whether the second Transformed Value is within a second range-of-vales; based on results of the multiple-parameter analysis, determining whether said user was positively affected or was negatively affected or was not affected by a particular intervention.

In some embodiments, step (a) comprises at least one of: (i) obtaining a digital representation of a typed text of the user; (ii) obtaining a printed item having printed thereon text of the user, and performing Optical Character Recognition (OCR) on said printed item; (iii) obtaining a handwritten item having handwritten thereon text of the user, and performing Optical Character Recognition (OCR) on said handwritten; (iv) obtaining an audio recording of the user, and performing speech-to-text conversion on said audio recording; (v) fetching a text sample of said user from a remote server.

Some embodiments comprise a non-transitory storage medium having stored thereon instructions that, when executed by a hardware processor, cause the hardware processor to perform a method as described above or herein. Some embodiments comprise a system having a hardware processor configured to perform a method as described above or herein.

Although portions of the discussion herein relate, for demonstrative purposes, to wired links and/or wired communications, some embodiments of the present invention are not limited in this regard, and may include one or more wired or wireless links, may utilize one or more components of wireless communication, may utilize one or more methods or protocols of wireless communication, or the like. Some embodiments may utilize wired communication and/or wireless communication.

The present invention may be implemented by using hardware units, software units, processors, CPUs, DSPs, integrated circuits, memory units, storage units, wireless communication modems or transmitters or receivers or transceivers, cellular transceivers, a power source, input units, output units, Operating System (OS), drivers, applications, and/or other suitable components.

The present invention may be implemented by using a special-purpose machine or a specific-purpose that is not a generic computer, or by using a non-generic computer or a non-general computer or machine. Such system or device may utilize or may comprise one or more units or modules that are not part of a "generic computer" and that are not part of a "general purpose computer", for example, cellular transceivers, cellular transmitter, cellular receiver, GPS unit, location-determining unit, accelerometer(s), gyroscope(s), device-orientation detectors or sensors, device-positioning detectors or sensors, or the like.

The present invention may be implemented by using code or program code or machine-readable instructions or machine-readable code, which is stored on a non-transitory storage medium or non-transitory storage article (e.g., a CD-ROM, a DVD-ROM, a physical memory unit, a physical storage unit), such that the program or code or instructions, when executed by a processor or a machine or a computer, cause such device to perform a method in accordance with the present invention.

Embodiments of the present invention may be utilized with a variety of devices or systems having a touch-screen or a touch-sensitive surface; for example, a smartphone, a cellular phone, a mobile phone, a smart-watch, a tablet, a handheld device, a portable electronic device, a portable gaming device, a portable audio/video player, an Augmented Reality (AR) device or headset or gear, a Virtual Reality (VR) device or headset or gear, a "kiosk" type device, a vending machine, an Automatic Teller Machine (ATM), a laptop computer, a desktop computer, a vehicular computer, a vehicular dashboard, a vehicular touch-screen, or the like.

The system(s) and/or device(s) of the present invention may optionally comprise, or may be implemented by utilizing suitable hardware components and/or software components; for example, processors, processor cores, Central Processing Units (CPUs), Digital Signal Processors (DSPs), circuits, Integrated Circuits (ICs), controllers, memory units, registers, accumulators, storage units, input units (e.g., touch-screen, keyboard, keypad, stylus, mouse, touchpad, joystick, trackball, microphones), output units (e.g., screen, touch-screen, monitor, display unit, audio speakers), acoustic microphone(s) and/or sensor(s), optical microphone(s) and/or sensor(s), laser or laser-based microphone(s) and/or sensor(s), wired or wireless modems or transceivers or transmitters or receivers, GPS receiver or GPS element or other location-based or location-determining unit or system, network elements (e.g., routers, switches, hubs, antennas), and/or other suitable components and/or modules.

The system(s) and/or devices of the present invention may optionally be implemented by utilizing co-located components, remote components or modules, "cloud computing"

servers or devices or storage, client/server architecture, peer-to-peer architecture, distributed architecture, and/or other suitable architectures or system topologies or network topologies.

In accordance with embodiments of the present invention, calculations, operations and/or determinations may be performed locally within a single device, or may be performed by or across multiple devices, or may be performed partially locally and partially remotely (e.g., at a remote server) by optionally utilizing a communication channel to exchange raw data and/or processed data and/or processing results.

Some embodiments may be implemented by using a special-purpose machine or a specific-purpose device that is not a generic computer, or by using a non-generic computer or a non-general computer or machine. Such system or device may utilize or may comprise one or more components or units or modules that are not part of a "generic computer" and that are not part of a "general purpose computer", for example, cellular transceivers, cellular transmitter, cellular receiver, GPS unit, location-determining unit, accelerometer(s), gyroscope(s), device-orientation detectors or sensors, device-positioning detectors or sensors, or the like.

Some embodiments may be implemented as, or by utilizing, an automated method or automated process, or a machine-implemented method or process, or as a semi-automated or partially-automated method or process, or as a set of steps or operations which may be executed or performed by a computer or machine or system or other device.

Some embodiments may be implemented by using code or program code or machine-readable instructions or machine-readable code, which may be stored on a non-transitory storage medium or non-transitory storage article (e.g., a CD-ROM, a DVD-ROM, a physical memory unit, a physical storage unit), such that the program or code or instructions, when executed by a processor or a machine or a computer, cause such processor or machine or computer to perform a method or process as described herein. Such code or instructions may be or may comprise, for example, one or more of: software, a software module, an application, a program, a subroutine, instructions, an instruction set, computing code, words, values, symbols, strings, variables, source code, compiled code, interpreted code, executable code, static code, dynamic code; including (but not limited to) code or instructions in high-level programming language, low-level programming language, object-oriented programming language, visual programming language, compiled programming language, interpreted programming language, C, C++, C#, Java, JavaScript, SQL, Ruby on Rails, Go, Cobol, Fortran, ActionScript, AJAX, XML, JSON, Lisp, Eiffel, Verilog, Hardware Description Language (HDL, BASIC, Visual BASIC, Matlab, Pascal, HTML, HTML5, CSS, Perl, Python, PHP, machine language, machine code, assembly language, or the like.

Discussions herein utilizing terms such as, for example, "processing", "computing", "calculating", "determining", "establishing", "analyzing", "checking", "detecting", "measuring", or the like, may refer to operation(s) and/or process(es) of a processor, a computer, a computing platform, a computing system, or other electronic device or computing device, that may automatically and/or autonomously manipulate and/or transform data represented as physical (e.g., electronic) quantities within registers and/or accumulators and/or memory units and/or storage units into other data or that may perform other suitable operations.

Some embodiments of the present invention may perform steps or operations such as, for example, "determining", "identifying", "comparing", "checking", "querying", "searching", "matching", and/or "analyzing", by utilizing, for example: a pre-defined threshold value to which one or more parameter values may be compared; a comparison between (i) sensed or measured or calculated value(s), and (ii) pre-defined or dynamically-generated threshold value(s) and/or range values and/or upper limit value and/or lower limit value and/or maximum value and/or minimum value; a comparison or matching between sensed or measured or calculated data, and one or more values as stored in a look-up table or a legend table or a list of reference value(s) or a database of reference values or ranges; a comparison or matching or searching process which searches for matches and/or identical results and/or similar results and/or sufficiently-close results, among multiple values or limits that are stored in a database or look-up table; utilization of one or more equations, formula, weighted formula, and/or other calculation in order to determine similarity or a match between or among parameters or values; utilization of comparator units, lookup tables, threshold values, conditions, conditioning logic, Boolean operator(s) and/or other suitable components and/or operations.

The terms "plurality" and "a plurality", as used herein, include, for example, "multiple" or "two or more". For example, "a plurality of items" includes two or more items.

References to "one embodiment", "an embodiment", "demonstrative embodiment", "various embodiments", "some embodiments", and/or similar terms, may indicate that the embodiment(s) so described may optionally include a particular feature, structure, or characteristic, but not every embodiment necessarily includes the particular feature, structure, or characteristic. Repeated use of the phrase "in one embodiment" does not necessarily refer to the same embodiment, although it may. Repeated use of the phrase "in some embodiments" does not necessarily refer to the same set or group of embodiments, although it may.

As used herein, and unless otherwise specified, the utilization of ordinal adjectives such as "first", "second", "third", "fourth", and so forth, to describe an item or an object, merely indicates that different instances of such like items or objects are being referred to; and does not intend to imply as if the items or objects so described must be in a particular given sequence, either temporally, spatially, in ranking, or in any other ordering manner.

Some embodiments may comprise, or may be implemented by using, an "app" or application which may be downloaded or obtained from an "app store" or "applications store", for free or for a fee, or which may be pre-installed on a computing device or electronic device, or which may be transported to and/or installed on such computing device or electronic device.

Functions, operations, components and/or features described herein with reference to one or more embodiments of the present invention, may be combined with, or may be utilized in combination with, one or more other functions, operations, components and/or features described herein with reference to one or more other embodiments of the present invention. The present invention may comprise any possible combinations, re-arrangements, assembly, re-assembly, or other utilization of some or all of the modules or functions or components that are described herein, even if they are discussed in different locations or different chapters of the above discussion, or even if they are shown across different drawings or multiple drawings.

While certain features of the present invention have been illustrated and described herein, many modifications, substitutions, changes, and equivalents may occur to those skilled in the art. Accordingly, the claims are intended to cover all such modifications, substitutions, changes, and equivalents.

What is claimed is:

1. A computer implemented method of determining efficacy of an intervention administered to a person, the method comprising using at least one computer processor for:
processing a digital representation of a first text, the first text is generated by the person before administering the intervention to the person, the processing comprising:
a) determining that a first text comprises N words;
calculating a first collection of Dynamic Word Entropy (DWE) values comprising N−K+1 values, K being an integer smaller than N; and wherein each DWE value is calculated for a respective $i^{th}$ text-segment of the first text, each text-segment consists of first K+i−1 words of the text;
applying at least one Transformation Function to the first collection of DWE values, and generating a first respective Transformed Value corresponding to the first collection of DWE values;
processing a digital representation of a second text, the second text is generated by the person after administering the intervention to the person, the processing comprising:
b) determining that a second text comprises N words;
calculating a second collection of Dynamic Word Entropy (DWE) values comprising N−K+1 values, K being an integer smaller than N; and wherein each DWE value is calculated for a respective $i^{th}$ text-segment of the second text, each text-segment consists of second K+i−1 words of the text;
applying at least one Transformation Function to the second collection of DWE values, and generating a second respective Transformed Value corresponding to the second collection of DWE values;
based on a difference between the first Transformed Value cone sponding to the first collection of DWE values and the second Transformed Value corresponding to the second collection of DWE values, determining whether the intervention had a positive, a negative, or a neutral effect on speech characteristics of the person.

2. The computer implemented method of claim 1, wherein the at least one Transformation Function comprises at least one of: average; median; variance standard deviation.

3. The computer implemented method of claim 1, wherein the intervention includes any one of:
medical treatment including administration of a medicine or a drug; learning session; psychotherapy treatment; and behavioral treatment.

4. The computer implemented method of claim 1, further comprising:
storing the collection of DWE values in a DWE table, wherein the DWE table comprises 1+N−K rows and wherein each row in the DWE table has a row-number denoted i, wherein each row in the DWE table comprises a Word Entropy value determined for the respective $i^t$ text-segment.

5. The computer implemented method of claim 1 further comprising:
generating the digital representation of the text, by any one of:
(i) obtaining a printed item having printed thereon text of the person, and performing Optical Character Recognition (OCR) on said printed item;
(ii) obtaining a handwritten item having handwritten thereon text of the user, and performing Optical Character Recognition (OCR) on said handwritten; and
(iii) obtaining an audio recording of the user and performing speech-to-text conversion on said audio recording.

6. A computer system comprising at least one processor operatively connected to a computer memory configured to:
process a digital representation of a first text generated by the person before administering the intervention to the person, the processing comprising:
a) determining that a first text comprises N words;
calculating a first collection of Dynamic Word Entropy (DWE) values comprising N−K+1 values, K being an integer smaller than N; and wherein each DWE value is calculated for a respective $i^{th}$ text-segment of the first text, each text-segment consists of first K+i−1 words of the text;
applying at least one Transformation Function to the first collection of DWE values, and generating a first respective Transformed Value corresponding to the first collection of DWE values;
processing a digital representation of a second text generated by the person after administering the intervention to the person, the processing comprising:
b) determining that a second text comprises N words;
calculating a second collection of Dynamic Word Entropy (DWE) values comprising N−K+1 values, K being an integer smaller than N; and wherein each DWE value is calculated for a respective ith text-segment of the second text, each text-segment consists of second K+i−1 words of the text;
applying at least one Transformation Function to the second collection of DWE values, and generating a second respective Transformed Value corresponding to the second collection of DWE values;
based on a difference between the first Transformed Value corresponding to the first collection of DWE values and the second Transformed Value corresponding to the second collection of DWE values, determining whether the intervention had a positive, a negative, or a neutral effect on speech characteristics of the person.

7. The computer system of claim 6, wherein the at least one Transformation Function comprises at least one of: average; median; variance standard deviation.

8. The computer system of claim 6, wherein the intervention includes any one of:
medical treatment; administration of a medicine or a drug; therapeutic treatment; learning session; focusing session; psychotherapy treatment; and behavioral treatment.

9. The computer system of claim 6, wherein the at least one processor is further configured to:
store the collection of DWE values in a DWE table, wherein the DWE table comprises 1+N−K rows and wherein each row in the DWE table has a row-number denoted i, wherein each row in the DWE table comprises a Word Entropy value determined for the respective $i^{th}$ text-segment.

10. The computer system of claim 6, wherein the at least one processor is further configured to generate the digital representation of the text, by any one of:
(i) obtaining a printed item having printed thereon text of the person, and performing Optical Character Recognition (OCR) on said printed item;

(ii) obtaining a handwritten item having handwritten thereon text of the user, and performing Optical Character Recognition (OCR) on said handwritten; and (iii) obtaining an audio recording of the user and performing speech-to-text conversion on said audio recording.

11. A non-transitory storage medium having stored thereon instructions that, when executed by a computer, cause the computer to perform a method comprising:
processing a digital representation of a first text generated by the person before administering the intervention to the person, the processing comprising:
a) determining that a first text comprises N words;
calculating a first collection of Dynamic Word Entropy (DWE) values comprising N−K+1 values, K being an integer smaller than N; and wherein each DWE value is calculated for a respective $i^{th}$ text-segment of the first text, each text-segment consists of first K+i−1 words of the text;
applying at least one Transformation Function to the first collection of DWE values, and generating a first respective Transformed Value corresponding to the first collection of DWE values;
processing a digital representation of a second text generated by the person after administering the intervention to the person, the processing comprising:
b) determining that a second text comprises N words;
calculating a second collection of Dynamic Word Entropy (DWE) values comprising N−K+1 values, K being an integer smaller than N; and wherein each DWE value is calculated for a respective $i^{th}$ text-segment of the second text, each text-segment consists of second K+i−1 words of the text;
applying at least one Transformation Function to the second collection of DWE values, and generating a second respective Transformed Value corresponding to the second collection of DWE values;
based on a difference between the first Transformed Value corresponding to the first collection of DWE values and the second Transformed Value corresponding to the second collection of DWE values, determining whether the intervention had a positive, a negative, or a neutral effect on speech characteristics of the person.

12. The computerized method of claim 1, wherein the intervention includes any one of: therapeutic treatment; and focusing session.

13. The computer system of claim 6, wherein the intervention includes any one of: therapeutic treatment; and focusing session.

14. A computer implemented method of generating text by a machine, the method comprising using at least one computer processor for:
executing a first text-generating computer program for automatically generating a first text and executing a second text-generating computer program for automatically generating a second text;
processing the first text, the processing comprises:
a) determining that the first text comprises N1 words;
calculating a first collection of Dynamic Word Entropy (DWE) values comprising N1−K+1 values, K being an integer smaller than N1; and wherein each DWE value is calculated for a respective $i^{th}$ text-segment of the first text, each text-segment consists of first K+i−1 words of the text;
applying at least one Transformation Function to the first collection of DWE values, and generating a first respective Transformed Value corresponding to the first collection of DWE values;
processing the second text, comprising:
b) determining that the second text comprises N2 words;
calculating a second collection of Dynamic Word Entropy (DWE) values comprising N2−K+1 values, K being an integer smaller than N2; and wherein each DWE value is calculated for a respective $i^{th}$ text-segment of the second text, each text-segment consists of second K+i−1 words of the text;
applying at least one Transformation Function to the second collection of DWE values, and generating a second respective Transformed Value corresponding to the second collection of DWE values;
based on a difference between the first Transformed Value cone sponding to the first collection of DWE values and the second Transformed Value corresponding to the second collection of DWE values, selecting a superior text-generating computer program from among the first text-generating computer program and the second generating computer program.

15. The computer implemented method of claim 14, wherein first text-generating computer program and second text-generating computer program are each machine learning computer programs.

16. The computer implemented method of claim 14, wherein the at least one Transformation Function comprises at least one of: average; median; variance standard deviation.

17. A computer system comprising at least one processor operatively connected to a computer memory configured to:
execute a first text-generating computer program for automatically generating a first text and execute a second text-generating computer program for automatically generating a second text;
process the first text, the processing comprises:
a) determine that the first text comprises N1 words;
calculating a first collection of Dynamic Word Entropy (DWE) values comprising N1−K+1 values, K being an integer smaller than N1; and wherein each DWE value is calculated for a respective $i^{th}$ text-segment of the first text, each text-segment consists of first K+i−1 words of the text;
applying at least one Transformation Function to the first collection of DWE values, and generating a first respective Transformed Value corresponding to the first collection of DWE values;
processing the second text, comprising:
b) determine that the second text comprises N2 words;
calculating a second collection of Dynamic Word Entropy (DWE) values comprising N2−K+1 values, K being an integer smaller than N2; and wherein each DWE value is calculated for a respective $i^{th}$ text-segment of the second text, each text-segment consists of second K+i−1 words of the text;
applying at least one Transformation Function to the second collection of DWE values, and generating a second respective Transformed Value corresponding to the second collection of DWE values;
based on a difference between the first Transformed Value cone sponding to the first collection of DWE values and the second Transformed Value corresponding to the second collection of DWE values, selecting a superior text-generating computer program from among the first text-generating computer program and the second generating computer program.

18. The system of claim 17, wherein first text-generating computer program and second text-generating computer program are each machine learning computer programs.

19. The system of claim 18, wherein the at least one Transformation Function comprises at least one of: average; median; variance standard deviation.

* * * * *

UNITED STATES PATENT AND TRADEMARK OFFICE
CERTIFICATE OF CORRECTION

PATENT NO. : 11,182,558 B2
APPLICATION NO. : 16/283773
DATED : November 23, 2021
INVENTOR(S) : Rybalov Page 1 of 1

It is certified that error appears in the above-identified patent and that said Letters Patent is hereby corrected as shown below:

In the Claims

At Column 23, Line 40, delete "cone sponding" and insert --corresponding--.

At Column 23, Line 60, delete "i<sup>t</sup>" and insert --$i^{th}$--.

At Column 24, Line 31, delete "ith" and insert --$i^{th}$--.

At Column 26, Line 19, delete "cone sponding" and insert --corresponding--.

At Column 26, Line 65, delete "cone sponding" and insert --corresponding--.

Signed and Sealed this
Fifteenth Day of March, 2022

Drew Hirshfeld
*Performing the Functions and Duties of the*
*Under Secretary of Commerce for Intellectual Property and*
*Director of the United States Patent and Trademark Office*